United States Patent [19]

Eisele et al.

[11] Patent Number: 5,218,203

[45] Date of Patent: Jun. 8, 1993

[54] ION SOURCE AND SAMPLE INTRODUCTION METHOD AND APPARATUS USING TWO STAGE IONIZATION FOR PRODUCING SAMPLE GAS IONS

[75] Inventors: Fred L. Eisele; Harald Berresheim, both of Norcross, Ga.

[73] Assignee: Georgia Tech Research Corporation, Atlanta, Ga.

[21] Appl. No.: 856,624

[22] Filed: Mar. 24, 1992

Related U.S. Application Data

[63] Continuation-in-part of Ser. No. 674,548, Mar. 22, 1991.

[51] Int. Cl.$^5$ .................................. H01J 49/26
[52] U.S. Cl. .................................. 250/288; 250/287; 250/282
[58] Field of Search ............ 250/288 R, 288 A, 287, 250/282, 283, 281, 286; 73/23.35

[56] References Cited

U.S. PATENT DOCUMENTS

| | | | |
|---|---|---|---|
| 3,621,239 | 11/1971 | Cohen | 250/41.9 |
| 3,626,178 | 12/1971 | Cohen | 250/41.9 |
| 3,626,180 | 12/1971 | Carroll | 250/41.9 |
| 3,668,383 | 6/1972 | Carroll | 250/41.9 |
| 4,378,499 | 3/1983 | Spangler et al. | 250/287 |
| 4,797,554 | 1/1989 | Blanchard et al. | 250/287 |

OTHER PUBLICATIONS

Hill, H. H., et al., Ion Mobility Spectrometry, 62 Anal. Chem. No. 23, 1201-(Dec. 1, 1990).

Primary Examiner—Jack I. Berman
Assistant Examiner—Jim Beyer
Attorney, Agent, or Firm—Deveau, Colton & Marquis

[57] ABSTRACT

A high pressure interface device for introducing sample ions to a drift tube, an ion detection means or a mass mobility measurement means, having an ion source ionization region containing an isolated ionization source, a sample introduction port, and a reaction region in which specific sample ion species are formed by reaction of sample molecules with selected ion source ions formed by radioactive bombardment of a sample gas by the ion source ions results in an ionized gaseous sample. When coupled to a ion or mass detection or measurement means, this invention makes possible detection sensitivities of trace sample species in the sub-parts-per-trillion range, and under proper condition does not need calibration.

25 Claims, 3 Drawing Sheets

ION SOURCE AND SAMPLE INTRODUCTION METHOD AND APPARATUS USING TWO STAGE IONIZATION FOR PRODUCING SAMPLE GAS IONS

STATEMENT OF RELATED APPLICATIONS

This application is a continuation-in-part of currently copending application Ser. .No. 07/674,548, filed on Mar. 22, 1991.

BACKGROUND OF THE INVENTION

1. Field of the Invention

The general field of this invention relates to a device for use in introducing ions and/or sample gases to ion detection and/or mobility measurement means in order to allow for greater detection sensitivities in the ion detection and/or mobility measurement means. The invention is used specifically as a coaxial laminar flow, flow tube to be used as an ion source introduction and concentration means in which specific ion species are reacted with a gaseous sample forming ionized species of the gaseous sample, which are then introduced into an ion mobility measurement and detection means. The ion source and introduction method results in a substantial increase in the sensitivity of the ion mobility and detection means. This invention also can be configured for use as a high pressure ion drift tube subsequent to an ion source flow reactor making possible the exclusive introduction of ionized sample molecules into a clean dry drift gas flowing through the drift tube.

2. Prior Art

The use of drift tubes and plasma chromatography for generating and detecting trace gases are known in the art. Typically, particular species of reactant ions are created within the drift tube and the various gate regions within the drift tube help to sort and detect the reactant ion by localizing the reactant ion by drift potential. Cohen, U.S. Pat. No. 3,621,239, discloses a plasma chromatography device in which positive or negative ions are formed by reactions between molecules of a trace gas substance and with primary ions. The positive or negative ions formed, commonly called secondary ions, are separated and detected within the drift cell by utilizing the difference in drift velocity or drift time of the ions of different masses.

Various configurations and alterations of the Cohen device are disclosed and claimed in U.S. Pat. No. 3,626,178, Carroll et al., U.S. Pat. No. 3,626,180 and Carroll U.S. Pat. No. 3,668,383. These four patents disclose improvements on plasma chromatography systems involving the formation of primary or reactant ions and reaction of the primary ions with molecules of trace substances to form secondary or product ions, which may be concentrated, separated, detected and measured by virtue of the difference of velocity or mobility of the ions in an electric field. In general, the inventions described in the above four patents comprise ionizing a host gas, such as air, to produce primary ions. These primary ions then are subjected to an electric drift field causing them to migrate to a reaction space. A sample or trace gas is introduced to the reaction space and the resulting collisions between the primary ions and the trace gas molecules produce secondary ions. The secondary ions, also subjected to the electric drift field are sorted in accordance with their drift velocity or mobility within a plasma chromatograph drift cell.

One disadvantage of the prior art apparatuses and methods for separating, detecting, and measuring trace gases is that the ionization of the host gas and the ionization of the trace gas occur within the drift cell itself. Unwanted bulk unionized host gas, unwanted unionized sample gas, and unwanted ions and reactant species therefore are present within the drift cell, thus preventing accurate measurements of the desired trace gas at levels in the sub-parts-per-trillion range. The unwanted bulk gas species and certain of the unwanted reactants and ion species flow through the drift cell into the measurement and detection devices. The presence of these unwanted components in the drift region results in chemical reactions in this region which prevent the obtaining of sharply focused ion arrival time peaks. Additionally, the structural configuration of prior art apparatuses may allow for host gas ions to travel through the drift cell, thus introducing impurities to the measurement and detection device. The structure of the prior art apparatuses also may allow the host gas ion/-trace gas ionization reactions to occur within the drift cell itself, resulting in a dramatic broadening of the arrival time spectra.

The use of plasma chromatography, or ion mobility spectrometry, also is known in the prior art. Hill, Jr. H.H., et al.. Ion Mobility Spectrometry, 62 Analytical Chemistry 23, pp. 1201a-1209a (Dec. 1, 1990), discusses the basic principle of ion mobility spectrometry as carried out using an ion drift tube. The drift tube disclosed in the Hill, Jr., et al. article discloses a counterflow drift tube in which a sample gas introduced to the drift tube is ionized within the drift tube. The ions created then are directed in the typical fashion to the measurement and detection device. As with the patents discussed above, the sample gases are ionized along the axis of the drift region in a non-preferential manner within the drift tube itself, thus introducing the possibility of a wide range of sample gas product ion species and extraneous ions created from other components of the sample gas or its fragments, thus preventing the detection and measurement sensitivity in the sub-parts-per-trillion range.

Atmospheric pressure chemical ionization mass spectrometry APCI/MS and plasma chromatography (PC) have to be extremely sensitive methods for detecting gas phase species at ultratrace levels. Currently, most of these methods are employed only for analysis of bulk phase samples. Therefore, their extreme sensitivity is rather limited to only those species having relatively high proton or electron affinities. The typical hierarchy of potentially stable product ion species present in gas samples limits the present applicability of chemical ionization detection methods to relatively few, very stable species. Sensitive detection of species having relatively low proton or electron affinities can be achieved by coupling atmospheric pressure chemical ionization with a technique, such as gas chromatography (GC), which separates the component(s) of interest in the sample matrix from interfering high affinity species. Thus, a potentially large number of species may be detected with extreme sensitivity using combined GC/AP-CI/MS or GC/APCI/PC. However, to this date, the powerful capabilities of these combinations of techniques have hardly been exploited. The present invention overcomes these disadvantages by offering a new ion source and sample introduction method for an ion drift tube and a new method of introducing ions of interest into a selectable pure, dry drift gas.

SUMMARY OF THE INVENTION

Therefore, there is the need for the method and apparatus described herein which will allow detection and measurement devices to detect and measure ion concentrations in the subparts-per-trillion range and below by preventing the introduction of unwanted gas species, unwanted reactant species and unwanted ion species into such detection and measurement devices. The present invention allows for the separation of the ionization of the buffer gas from the reaction between the buffer gas ions and the sample gas and further separates both of these prior to the drift region, thus significantly reducing the amount of unwanted bulk gas, unwanted reactant species, and unwanted ion species from entering the drift region and proceeding into the detection and measurement devices.

The invention generally is a device which allows the introduction of a selected ion and a gaseous sample to a detection and measurement means. The invention comprises a novel high pressure flow tube device which can act as an ion source flow reactor, into which a gaseous sample is introduced which reacts in one reaction region with a previously introduced specific ion species, created by an ion source gas which is ionized by a low intensity radioactive source in a separate ionization region. The sample gas is forced to encounter and react with the ion source species ions, which can be specifically selected for use with the chosen sample gas. An electric field is applied to move only the ionized sample species and not any other ion or neutral species into the flow tube reactor. The high sensitivity of the present apparatus is achieved by allowing each specifically prepared ion source ion species to undergo many billions of collisions with the sample gas resulting in a high specific ionization efficiency. The now ionized sample gas species is directed into the central drift tube gas flow separate from the reaction regions, where it can be gated into a flow-opposed drift region until a sufficient or desired quantity of the particular sample ion species is accumulated in the drift tube, after which it can be gated into the drift region and measurement devices.

The ion sources gas flow, the sample gas flow, and the drift gas flow, generally are coaxial and parallel with each other, although not necessarily codirectional. Typically, however, the ion source gas flow, the sample gas flow, and the drift gas flow are codirectional upon entering the present apparatus. In one preferred embodiment, following the reaction of the ion source gas ions with the sample gas to create sample gas ion species, the extraneous unionized ion source gas and sample gas are exhausted while the sample gas ion species are forced to enter the separate drift tube region. In this embodiment, the sample gas ion species and the drift gas continue to flow co-directionally. In a second preferred embodiment, after the ion source gas has reacted with the sample gas to form the sample gas ion species, the sample gas ion species enter the separate drift region and are forced to flow in the opposite direction of the drift gas.

The ion source gas, the sample gas, and the drift gas, may be directed through a flange with uniformly spaced holes, and then through one or more turbulence-reducing screens. The flange and/or screens help to establish a uniform and laminar flow pattern in the three gas flows, prior to entering the reaction region of the apparatus. The ion source gas flow, the sample gas flow, and the drift gas flow, flow coaxially and are separated from each other by separating walls configured to allow a drift gas to flow centrally, contained within the inner separating wall, the sample gas to flow as a sheath around the drift gas, but separated therefrom by the inner separating wall, the sample gas being contained within a middle separating wall. The ion source gas flows as a sheath outside of the sample gas and separated therefrom by the middle separating wall, the ion source gas being contained by the outer separating wall.

The ion source gas is ionized in the initial ionization region and subsequently introduced to another reaction region by an introduction plenum region located peripherally about the reaction region, and is separated from the sample gas introduction means via the middle separating wall, forming an outer plenum for the introduction of the sample gas and an inner plenum for the ionization and introduction of the ion source gas. The ionized ion source gas is introduced to the sample gas by electric fields which guide the ion source gas ions radially inward to encounter and react with the sample gas, thus creating the sample species ions. The sample species ions continue to be forced radially inward by an electric field to a plenum through which the drift gas is flowing.

In the codirectional flow embodiment, the sample species ions, after entering a drift gas flow plenum, flow in a direction codirectional with a drift gas, and into a drift tube introduction plenum. In the flow-opposed embodiment, the sample species flow in a direction counter to the drift gas flow, toward the drift tube region which is located upstream (in the relation to the flow of drift gas) of introduction. In the codirectional flow embodiment, the drift tube introduction plenum has a smaller diameter than the drift gas introduction plenum diameter, thus allowing unionized ion source gas, unionized sample gas, and the outer portion of the drift gas to be exhausted radially outward through an exhaust port without entering the drift tube introduction plenum. Thus, only drift gas and sample gas ion species are introduced to the drift tube. In the flow-opposed embodiment, the unionized ion source gas and the unionized sample gas continue to flow in the same direction, a direction opposite from the relative location of the drift tube, and are exhausted. The sample species ions are then forced by electric fields to flow in a direction opposite the drift gas to the drift tube.

The sample gas, generally a bulk sample, but often the eluent from a gas chromatograph, after reacting with the single reactant ion species (the ionized ion source gas), forms relatively stable sample species ions and trace gas atoms or molecules. The concentration of sample species ions formed is relatively typically small ($<10$) compared to the concentration of initial ion source gas ions. Since the reaction times, the reaction rate constant for the reaction of the ion source gas ion/sample species of interest, and the concentration ratio of ion source gas ion/sample ion are either known or measurable, the sensitivity of the above apparatus can be both known and fixed at predetermined values for any specific compound as long as the initial ion source gas ion remains the primary species present in the ion spectrum. The flow tube reactor cell typically operates at pressures on the order of one atmosphere or higher to increase sensitivity.

A drift tube can be located within, prior to or subsequent to the flow reactor region. The construction of the drift tube is generally conventional in nature, comprising one or more entrance (shutter) and exit grids to assist in gating the ions, and to make an ion pulse if necessary. Guard grids at the end of the drift tube typically are employed to shield the collecting plate, which collects the sample species ions for measurement, from changing electric fields, and guard rings maintain a uniform field throughout the drift region.

The present invention does not suffer from the difficulties encountered with previous ion source introduction techniques and apparatuses because it does not directly ionize the gas being sampled. Instead, ion species formed from an ion source gas are physically separated from most metastable or radical species before being allowed to interact with the gas sample to be analyzed. The present technique also differs in that it uses a single selectable specific core ion source species to react with the sample compound to be measured. If the species to be detected forms a sufficiently stable ion such that once formed it will not react further, then the present device often can be operated on a continuous basis; that is, without the requirement for a discrete, non-continuous sample introduction to the device from a pre-separating means such as a gas chromatograph. This is possible as long as the initial reactant ion can be maintained as the predominant ion species present by: (1) choosing an ion gas which produces sufficiently stable reactant ion; (2) reduction of reaction time; (3) sample dilution; or (4) some combination of the above possibilities.

When compared to the prior art methods for ion introduction to plasma chromatographs, the present invention offers several advantages including the ability to introduce a single, selected reactant ion species. These advantages provide for the product ion to be formed by a single known reaction. If the initial reactant ion concentration is kept high enough, then the ratio of the product ion concentration to the initial ion concentration can be used to measure the concentrations of the ions, in which case the present apparatus need not be calibrated for each measurement. Further, these advantages allow the user to simplify the spectrum so that in some cases only higher proton or electron species will be present, thus eliminating interferences.

Additionally, the present invention offers the advantage of providing a means of moving both reactant and product ions into a pure, dry, selectable drift gas without the need for physical constraints, such as membranes to remove water. The elimination of such physical constraints also allows large, sharper, and more reproducible mobility peaks. In a flow opposed drift configuration, the present invention makes possible an increase in the ion concentration of the ions in the mobility range of interest. Higher ion concentrations allow the ion mobility measurement and detection means to measure the desired ion concentration with greater sensitivity.

Accordingly it is an object of the present invention to provide a means for introducing ions and samples to ion detection or mobility measurement means.

It is another object of the present invention to provide a means for introducing ions and samples which allows an increase in the detection sensitivity of ion detection or mobility means.

A further object of the present invention is to provide a means for introducing ions and samples which can act as an interface between a gas injection means and an ion detection or mobility measurement means.

Yet another object of the present invention is to provide a means for introducing ions and samples obtained from a gas chromatograph to a mass spectrometer or plasma chromatograph.

Still another object of the present invention is to provide a means for introducing ions and samples which allows for the obtainment of sharply focussed ion arrival time peaks.

Another object of the present invention is to provide a means for introducing ions and samples which allows reaction free and cluster free ion drift.

It is still another object of the present invention to provide a means for introducing ions and samples to ion detection or mobility measurement means which is able to utilize a variety of drift gases.

Still another object of the present invention is to provide a means for introducing ions and samples to a flow-opposed drift tube.

Another object of the present invention is to provide a means for introducing ions and samples which increases the ion concentration of the species of interest.

Yet another object of the present invention is to provide a means for introducing ions and samples which allows for increased separation of ion mobilities near the mobility of interest.

These objects, and other objects, features and advantages of the present invention, will become apparent to one skilled in the art when the following Detailed Description of a Preferred Embodiment is read in conjunction with the accompanying Figures, in which like reference numerals represent corresponding parts throughout the several drawings.

DETAILED DESCRIPTION OF A PREFERRED EMBODIMENT

1. General Apparatus

Figure 1:
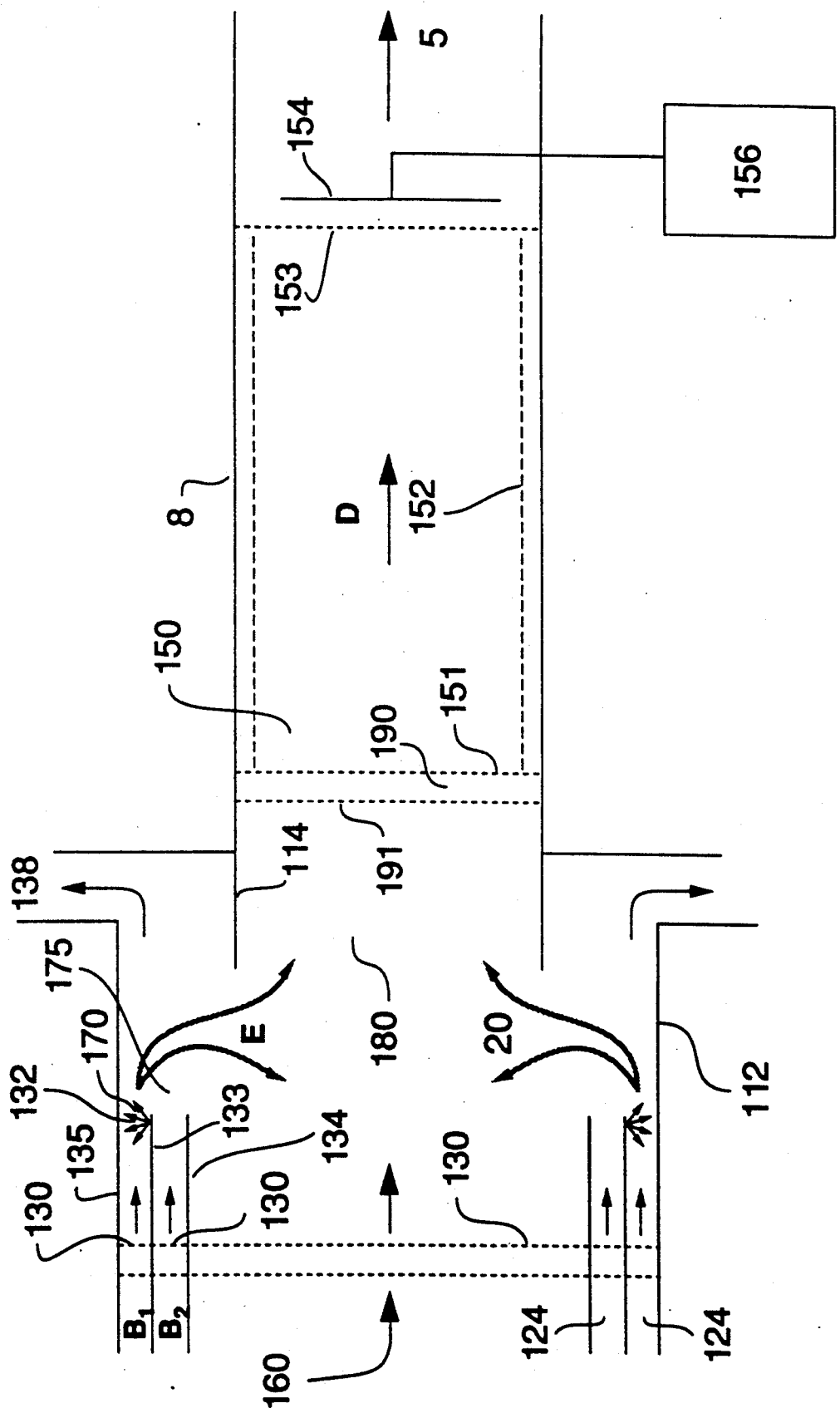
FIG. 1 is a schematical cross-section of the apparatus of the present invention showing a co-directional flow embodiment through a drift region.
Figure 2:
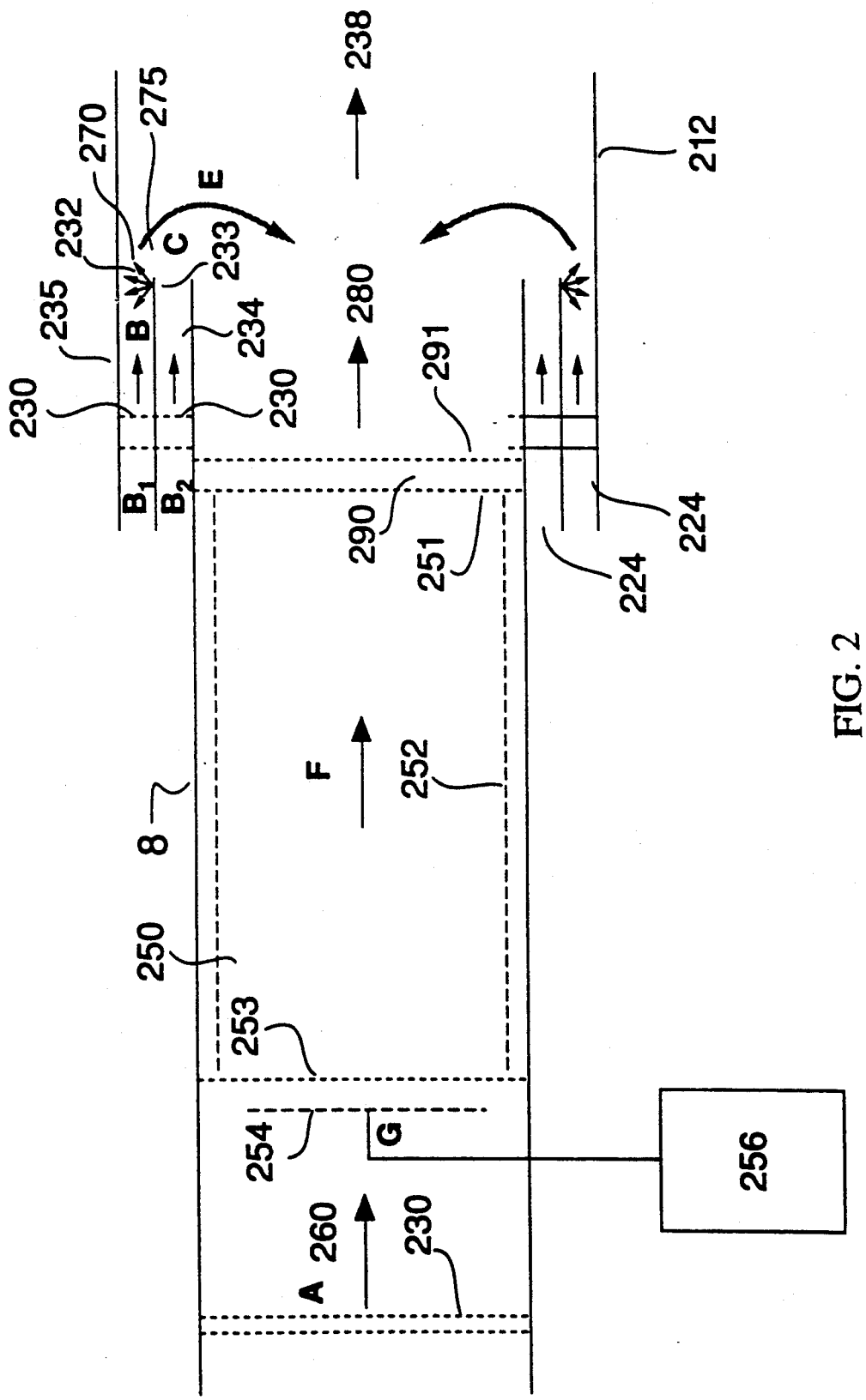
FIG. 2 is a schematical cross-section of the present invention showing an flow-opposed embodiment through a drift region.

Referring now to FIGS. 1 and 2, the introduction apparatus of the present invention generally comprises two separate sections, a first section comprising two distinct reaction regions and a second section comprising a drift tube and detection and measurement means. The first reaction region of the first section comprises a high pressure flow tube 112, 212, in which sample ion species are formed by the bombardment of an ion source gas $B_1$ by either alpha or beta bombardment 132, 232 to create ion source ions. In the second reaction region of the first section, the subsequent reaction of the ion source ions with a sample gas $B_2$, results in the production of sample gas ions. These sample gas ions then are introduced to the second section where they are sorted by a drift tube 150, 250 for direction and/or preconcentration and then introduced to the detection and measurement means. The separation of the first section comprising the reaction regions from the second section comprising the drift tube and the detection and measurement means provides a new and unique method and configuration for minimizing or eliminating unwanted components and impurities from being introduced to the drift tube 150, 250 and the detection and measurement means. When used in relation to the present apparatus, the term high-pressure is defined as pressures on the order of magnitude of one atmosphere or higher.

In general, several of the various parts of apparatus 112, 212 are electrically conducting, although insulated from each other, to allow for the production of electric fields E and have smooth bores to minimize gas turbulence. The apparatus 112, 212 also is of sufficient diameter that diffusion of the ion species between the walls and center of the apparatus 112, 212 (or the converse) is not significant in the time required for the sample gas to travel to the drift tube region 150, 250. Although the diameter of the apparatus 112, 212 is not critical, the diameter is to a certain extent dependent on the residence time necessary for sufficient reaction of the sample gas with the ion species contained in the buffer gas.

A cryogenic trap may be used to purify the ion source gas and the drift gas prior to introduction to the apparatus 112, 212. The cryogenic trap is generally a high pressure liquid nitrogen trap (about 20 psi) which can be heat-cleaned for 24–48 hours or longer. Using this trap, the presence of polar and high electron and proton affinity species in the ion source and the drift gas can be reduced down to the low apt range. The ion source gas and drift gas optionally may be photolyzed subsequent to the cryogenic trap.

The ion source gas, the sample gas, and the drift gas enter the apparatus 112, 212 through turbulence reducing means, such as a back flange (not shown) at the proximal end of the apparatus 112, 212 having a series of uniformly spaced holes to more uniformly distribute the gases, and metal turbulence-reducing screens 130, 230, or other suitable means to establish a uniform and laminar flow pattern. The exact mesh size of the turbulence-reducing screens 130, 230 is not critical as long as a mesh with a relatively regular pattern is used. A finer mesh will help reduce turbulence. Other methods which form a laminar gas flow within a short distance are suitable, such as the use of a plurality of holes in the back flange, the use of mesh substitutes, or the use of a laminar flow creating region which allows the establishment of a laminar flow prior to introduction of the gases to the apparatus 112, 212.

Within the first section of the apparatus 112, 212, the ion source gas enters the ionization region (the first reaction region) 170, 270 where it is ionized by a radioactive source 132, 232 such as an alpha or beta emitter coated on a cylinder or ring concentric with the inside of the apparatus 112, 212. For example, a radioactive coating of Nickel-63 on the order of 10 milli-curies, or a radioactive coating of Americium ($Am_{241}$) of 100 micro-curies may be used. Various known radioactive sources which are sufficient to create the selected level of ionization are acceptable. It is preferable to have a very low intensity radioactive source which produces a stable emission, and is just strong enough to ionize the ion source gas with minimal formation of metastable or radical species. In this regard, corona sources are less desirable. X-ray sources also are suitable. It is important that the ionization of the ion source gas occurs in an isolated region where no sample gas is present, but preferably just prior to encountering the sample gas.

The sample gas is introduced to the apparatus 112, 212 by flowing the sample gas coaxial with and radially inside the flow of the ion source gas, but separated therefrom by middle separating wall 133, 233. The sample gas does not encounter the ion source gas until after the ion source gas has been ionized by the radioactive source 132, 232 and enters the reaction region 175, 275 (the second reaction region). An electric field E forces the ion source gas ions through the flow path of the sample gas. At this point, the sample gas mixes rapidly with the ion source ions within a few ($<10$) millimeters from the end of the middle separating wall 133, 233 and the inner separating wall 134, 234 which are coextensive, and react with the sample gas in the second reaction region to create sample gas ions. It is important that the second reaction region is separate and distinct from the first reaction region such that the sample gas mixes and reacts for the most part only with a single specifically prepared ion source ion species.

The sample gas ions are directed by the electric field E from the first section of the apparatus 112, 212 into the central region or drift tube introduction plenum 180, 280 and into the drift tube region 150, 250, both located in the second section of the apparatus 112, 212. Remaining ion source gas and sample gas not ionized is exhausted from the first section of the apparatus 112, 212 through exhaust port 138, 238, without ever entering the second section of the apparatus 112, 212.

The drift gas is typically an inert gas used to create a positive flow through the second section of the apparatus 112, 212, including the drift tube region 150, 250. Gases such as nitrogen are suitable; gases with low reactivities with the sample gas ions are desired. Thus, the specific drift gas is chosen to be compatible (i.e., nonreactive) with the sample gas ions. The drift gas enters the apparatus 112, 212 through the drift gas plenum 160, 260, which basically defines the central, longitudinal portion of the apparatus 112, 212. As can be seen from FIGS. 1 and 2, the drift gas defines a central flowing gas around which the sample gas and ion source gas flow in sheath-like configurations, with the sample gas being separated from the drift gas by inner separating wall 134, 234, the ion source gas being separated from the sample gas by middle separating wall 133, 233, and the outer separating wall 135, 235 acting to contain the ion source gas. In the cocurrent flow embodiment shown in FIG. 1, the drift gas encounters the central region or drift tube introduction plenum 180 and the sample gas ions prior to entering the drift tube region 150, as explained in more detail below. In the flow-opposed embodiment shown in FIG. 2, the drift gas encounters the drift tube region 250 prior to encountering the central region or drift tube introduction plenum 280 and the sample gas ions, also as explained in more detail below.

A complex sample matrix such as ambient air may contain many gaseous components and it may be desirable to measure the quantity of only one of the gaseous components. The ion source gas can be or is sometimes selected by choosing a specific gas which, when ionized by the radioactive source 132, 232, will selectively react with the desired gaseous component of the sample gas, while reaction with most of the other gaseous components contained in the ambient air sample is negligible. As a result of the separation of the ion source gas introduction $B_1$ and the sample gas introduction $B_2$, ideally a single specific ground state ion species can be produced from the sample gas. By using the known or measurable reaction rate between the ion source gas and the gaseous component of the sample gas, the quantity of the sample gas component of interest can be determined from the ratio of reactant (ion species formed in the ion source) ion/product (formed from sample gas) ion concentration, the reaction rate constant, and reaction time. In this manner, only two ion species are involved in the measurement, one being the sample component of interest. A major depletion of the reactant ion signals that the sample ion production is no longer linear. This is typically the case when other reactive species in the sample gas are at too high a concentration, making it necessary to adjust flow conditions or sample gas purity.

The drift tube region 150, 250 into which the sample gas ions are introduced is known in the art and typically comprises the conventional retaining grids: one or more gating or shutter grids 151, 251, one or more guard grids 153, 253, and guard rings 152, 252. The sample species ions entering the central region or drift tube introduction plenum 180, 280 continue to travel through the apparatus 112, 212, and encounter the drift tube region 150, 250. The gating grids 151, 251 allow the sample ions to enter the drift tube region 150, 250. The general drift tube described in the Hill, Jr., et al. article cited above is suitable for use with the present apparatus 112, 212 and is incorporated herein by this reference. However, the Hill, Jr., et al. drift tube only can function as part of the second section of the present apparatus 112, 212, and the first section of the present apparatus 112, 212, must be substituted to provide the novel and unique sample gas and buffer gas introduction means and methods and the first and second reaction regions. The use of a very dry (less than about 1 ppb $H_2O$), clean ion source gas and drift gas is desired as such dry, clean gases will, if used in conjunction with a dry sample gas, prevent or minimize reactions in the drift region. The cryogenic trap helps achieve this.

2. Specific Preferred Apparatus

Turning now to FIGS. 1 and 2, alternate embodiments of the preferred apparatus 112, 212 are shown. Corresponding parts in FIGS. 1 and 2 are denoted by adding the numerals 1 and 2, respectively, before the corresponding XX numerals. The embodiment shown in FIG. 2 is identical to the embodiment shown in FIG. 1 with the exception of the placement of the drift tube region 150, 250 and drift gas entrance region 190, 290. FIG. 1 represents a co-current flow apparatus 112 in which the sample ions drift in the same direction as the drift gas. FIG. 2 represents a flow-opposed apparatus 212 in which the sample ions drift in the opposite direction as the drift gas.

a. Co-Current Flow Apparatus

In the embodiment shown in FIG. 1, the co-current apparatus 112 is shown. The sample gas, indicated by the arrow labeled $B_2$, is introduced into the first section of the apparatus 112 through a central input sheath port located between inner separating wall 134 and middle separating wall 133. The ion source gas, indicated by the arrow labeled $B_1$, enters the first section of the apparatus 112 through an input sheath port located between middle separating wall 133 and outer separating wall 135. The drift gas, indicated by the arrow labeled D, is introduced into the second section of the apparatus 112 through the central tubular section of the apparatus 112 defined by inner separating wall 134. The three gases flow co-currently at approximately the same flow rates.

Prior to encountering each other, it is preferred that the three gases are in laminar flow. Typically, the three gases pass through a flange with uniformly spaced holes (not shown) at the entrance end of the apparatus 112 and then through turbulence-reducing screens 130 to create a more laminar flow of the gases. The ion source gas now enters the ionization region 170, where the ion source gas is ionized by the radioactive source 132 in the first reaction region.

The gas input zone 124 shown is separated into two or more regions, including at least one ion source gas input $B_1$ and the sample gas input $B_2$ separated by middle separating wall 133. The ion source gas passes by the radioactive source 132, typically located on the outer surface of middle separating wall 133, but which can be located anywhere in the ionization region 170, or on the inner surface of outer separating wall 135. Ion source gas ions produced in the ionization region 170 exit ion source gas introduction port $B_1$, and are directed to the second reaction region 175 by an electric field E. Unionized ion source gas is exhausted from the apparatus 112 through exhaust port 138.

The sample gas exits sample gas introduction port $B_2$ and encounters, typically in less than 10 mm from the ends of coextensive middle separating wall 133 and inner separating wall 134, the ion source ions in the second reaction region 175. The ion source ions react with the sample gas in reaction region 175 to produce sample gas ions. The sample gas ions are directed out of the first section and into the central region or drift tube introduction plenum 180 of the second section by an electric field E. Unionized sample gas is exhausted from the apparatus 112 through exhaust port 138, without ever entering the second section (drift tube).

The drift gas enters the second section of the apparatus 112 through drift gas introduction plenum 160 located within the volume bounded by inner separating wall 134. Structurally, drift gas introduction plenum 160, sample gas introduction port $B_2$ and ion source gas introduction port $B_1$ are generally coextensive. Contiguous to plenum 160 is drift tube introduction plenum 180, and contiguous to port $B_2$ and radially circumferencing plenum 180 is reaction region 175. Contiguous to reaction region 175 and the radially outermost portion of plenum 180 is exhaust port 138, which has as its outer wall outer separating wall 135 and as its inner wall drift tube wall 114. Drift tube wall 114 extends inwardly in plenum 180 opposite plenum 160 and has a diameter at most equal to and preferably less than the diameter of plenum 160 such that the unionized ion source gas and sample gas, in their generally laminar flow, will flow directly into exhaust port 138 to be removed from the apparatus 112 and prevented from entering the tube region 150.

The electric potential difference is created between the various separating walls 133, 134, 135 and the drift tube wall 114, which are electrically insulated from each other, to create electric fields E to cause the ion source gas ions to drift into the path of the sample gas in the reaction region 175, and to cause the subsequently created sample gas ions to drift into the drift tube introduction plenum 180. Thus, after being ionized in ionization region 175, the sample gas ions are forced into plenum 180 by electric fields E where they are positioned to enter the drift tube region 150. The positioning of radioactive source 132 along middle separating wall 133 requires the use of different electric fields E, depending on the selected position of radioactive source 132 on middle separating wall 133.

The drift gas serves several purposes. First, the drift gas presents a non-reactive atmosphere through which the sample gas ions travel in the drift tube region 150. Second, the drift gas helps maintain the apparatus 112 at high pressure, reducing radial diffusion of the sample gas ions. Third, the drift gas, preferably being extremely pure, such that when the sample gas ions transfer into the drift gas, they do not react, thus allowing sharply peaked ion arrival time spectrum to be measured. Fourth, the drift gas creates a positive flow condition within the apparatus 112 and helps ensure that the unionized ion source and sample gases are exhausted through exhaust port 138; the outermost portion of the drift gas exhausts through exhaust port 138 because drift tube region 150 has a smaller diameter than drift gas introduction plenum 160. However, the majority of the drift gas, together with the sample gas ions and some ion source gas ions, enter the drift tube region 150 and flows toward the detection and measurement means represented by collecting grid 154 and fast electrometer 156. Drift tube region 150 otherwise is conventional in construction and operation.

b. Flow-Opposed Apparatus

In the embodiment shown in FIG. 2, the flow-opposed apparatus 212 is shown. The sample gas, indicated by the arrow labeled $B_2$, and the ion source gas, indicated by the arrow labeled $B_1$, are introduced to the apparatus 212 in substantially the same manner as described in reference to FIG. 1 and the disclosure of the co-current flow apparatus 112. The structure and operation of the flow-opposed apparatus 212 are similar to that of the co-current flow apparatus 112 disclosed above in connection with FIG. 1 with the major difference being that the drift tube region 250 is located prior to and within drift tube ion introduction plenum 280 and prior to drift gas introduction plenum 260. Thus, sample gas ions, after being forced into the drift tube introduction plenum 280 by an electric field E, must travel upstream relative to the drift gas flow to enter the drift tube region 250. In all other aspects, the operation of flow-opposed apparatus 212 is similar to that of co-current flow apparatus 112. Exhaust port 238 now encompasses the entire end of the apparatus 212. Also, measurement means 254 must be a relatively optical transparent grid that does not cause drift gas flow to become turbulent.

c. Drift Region

The flow opposed drift region 190, of the apparatus 112, 212 defines the entrance to the drift tube region 150, 250. Drift region 150, 250 is typical for drift cells and generally comprises one or more shutter grids 151, 251 and the area bound by such shutter grids 151, 251, 153, 253. The general purpose of flow opposed drift region 150, 250 is to allow the sample ion species of interest to be gated to the drift tube region 150, 250 and to be measured later by the measurement and detection means. Prior to the drift region 150, 250, region 190, 290 in the present invention comprises an addition grid 191, 291 so that the apparatus can be operated in several modes including, for example, a pulse mode (normal) or a build-up mode.

In the open mode, the shutter grids 151, 191, 251, 291 allow all, ;of the sample species ions to travel through the flow opposed drift region 190, 290 and into the drift tube region 150, 250. The build-up mode is used when the amount of sample species ions makes up only a small fraction of the total ion concentration to concentrate the amount of sample species ions within the flow opposed drift region 190, 290 such that a greater quantity of sample species ions can be gated to the drift tube region 150, 250 at one time, allowing for better detection and measurement by the detection and measurements means. In the build-up mode, a first shutter grid 191, 991 is set at an appropriate electric potential such that the sample species ions of interest will travel through the first shutter grid 191, 291. A second shutter grid 151, 251 is set at an electric potential such that the uniform electric field between first shutter grids 191, 291 and second shutter grids 151, 251 imparts a drift velocity to the ion species of interest that is equal in magnitude, but opposite in direction, to that of the gas flow in that same region 190, 290. This electric field configuration prevents the selected sample species ions from entering the drift tube region 150, 250. It is preferable that the gas flow be laminar and approximately plug flow. Thus, a buildup of only the sample species ions of interest occurs within the flow opposed drift region 190, 290. The pulse mode can then be used in conjunction with the build-up mode in which sample species ions of interest are alternately built up within the flow opposed drift region 190, 290 by applying appropriate electric potential to the shutter grids 151, 191, 251, 291, and then forcing the sample species ions of interest into the drift tube region 150, 250. By using the pulse mode, in conjunction with the buildup mode, a more sensitive detection and measurement of the sample species of ions of interest can be made than using the pulse mode alone.

The following description of the flow opposed drift region 190, 290 is made with reference to the flow-opposed apparatus 212 shown in FIG. 2. However, this description, is applicable to both the flow-opposed apparatus 212 flow opposed drift region 290 and the co-current flow apparatus 112 flow opposed drift region 190 as they are otherwise substantially identical.

The flow-opposed drift region 290 improves the separation of sample neutral species from the drift tube region 250, while minimizing the requirement that laminar flow be maintained in the ion source gas and sample gas flows and that no mixing of ion source gas, sample gas and drift gas occur. A gas flow velocity exactly opposite in direction but equal in magnitude to the electrical drift velocity of the ion species of interest can be used to increase the concentration of the ion species. The drift gas has a constant velocity $V_g$ through the flow opposed drift region 290. An electrical drift field is created in the flow opposed drift region 290 by applying different electric potentials to entrance grid 291 shutter grid 251 to create a drift velocity $V_d$ of the sample gas ions through the flow opposed drift region 290 in the direction opposite of $V_g$. Without the drift field, the sample gas ions would tend to flow codirectionally with the drift gas.

It is important that the second section, comprising the drift tube introduction plenum 180, 280, the flow opposed drift region, 190, 290, the drift tube region 150, 250, the drift gas introduction region 160, 260, the detection and measurement means 154, 254, 156, 256, and the associated grids and fixtures be separate and distinct from the first section, comprising the sample introduction regions and the reaction regions. By keeping these two sections separate and distinct, the introduction of unwanted bulk gas, unwanted reactant species and unwanted ions to the detection and measurement means can be minimized or avoided. Additionally, when determining the proper potential to apply within the shutter grids 151, 191, 251, 291, it is important that the potentials be weak not to effect the electric field E directing the sample species ions from the first section into the flow opposed drift region 190, 290. For example, it is important to have the electric potential on the grids 151, 191, 251, 291 be weak enough such that the electric field E does not cause the ions to be lost on the grids 151, 191, 251, 291, but allows the ions, to travel through the grids 191, 291, into the flow opposed drift region 190, 290. If the electric field E terminates on the grids 151, 191, 251, 291, the sample species ions will follow the electric field E and hit the grid 151, 191, 251, 291, which is to be avoided.

With a drift gas velocity $V_g$ equal to or preferably very slightly below the drift field velocity $V_d$, but in opposite directions, the sample gas ions are essentially stationary within the flow opposed drift region 290. With a drift field velocity $V_2$ greater than the drift gas velocity $V_g$, sample gas ions can be forced into the drift tube region 250. By varying the potentials on grids 251, 291, the concentration of sample gas ions can be built up within the flow opposed drift region 290, and released at a selected time to the drift tube region 250 and the ion detection and measurement means for more sensitive measurement. This essentially is a preconcentration means. This technique can be used to allow only species with a specific ion mobility which make up only a small fraction of the total ion concentration to be accumulated and stored in a flow opposed drift region and later released, to the exclusion of species with differing ion mobilities that either pile up at and are lost to grid 291 or continuously pass through the grids 291, 251 and thus have no discrete arrival time.

3. Operation

The apparatus 112, 212 may be calibrated for each sample species desired to be detected by determining the reaction parameters (reaction rates, reaction times, reaction temperatures, etc.) for the desired species. Each ion source ion has a different reaction rate constant and electron or proton affinity relative to the sample gas ion and may require different reaction parameters, such as, for example, reaction time, apparatus temperature, feed rate of sample gas and quantity and feed rate of ion source ion. Once the apparatus 112, 212 is calibrated for a specific sample ion, it can be left at that calibration for detection of that sample ion because the calibration depends not on ion detection sensitivity but on the ratio of two ion concentrations. Alternatively, standard plasma chromatograph calibration techniques can be used.

This ion source and sample introduction apparatus 112, 212 design offers advantages including the ability to select a single reactant ion species, the elimination of interferences from reactions with metastables and radicals formed in the ion source region and from the ion source gas as well as trace gases used to form specific ions, the spacial separation of the ion source region and the reaction region, and the creation of an effectively wall-less reactor. In addition, this ion source and sample introduction apparatus 112, 212 design makes possible the introduction of exclusively ionized species into a clean, dry drift gas, which in turn makes possible ion mobility measurements unperturbed by ongoing ion reactions or ion cluster formation in the drift region 190, 290. The use of two separate sections, a first section comprising gas introduction regions and reaction regions and a second section comprising the drift tube and detection and measurements means, allows the transfer of only ions, and not of bulk gas, into the drift tube and detection and measurement means, thus accomplishing the main objective of the present invention, that being to allow the detection and measurement of ions in the subparts-per-trillion range and below. Additionally, only transferring ions which will not react with each other (because they are of the same charge) further helps to increase the purity of the sample species ions introduced to the detection and measurement means. This ion source and sample introduction apparatus 112, 212 design increases both the sensitivity and the specificity of a plasma chromatograph by reducing background signal and providing larger and sharper ion arrival time peaks. The present apparatus 112, 212 also makes possible the measurement of ion mobility spectra using preselected drift gases other than nitrogen, including the successive use of several different drift gases.

To achieve greatest detection and measurement, the flow opposed drift tube region 150, 250 and drift region 190, 290 gate electronics should be synchronized with the sample introduction. The major advantage of using the present device coupled to a plasma chromatograph, corresponding to drift tube region 150, 250, rather than to a mass spectrometer, is its relative simplicity and low cost. No vacuum requirements, a greater flexibility for field use, and a relatively high potential for further miniaturization are but three of many advantages. The apparatus 112, 212 is particularly useful for separating one light mass sample species from heavy mass sample(s).

Figure 3A:
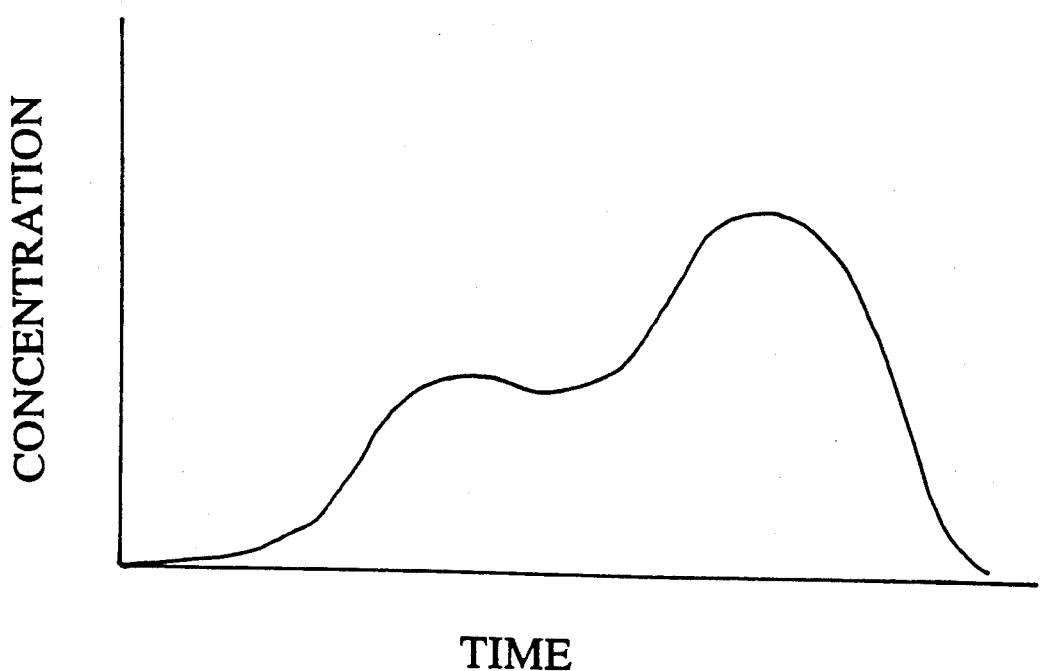
FIG. 3a is a peak diagram representative of the output from the prior art.
Figure 3B:
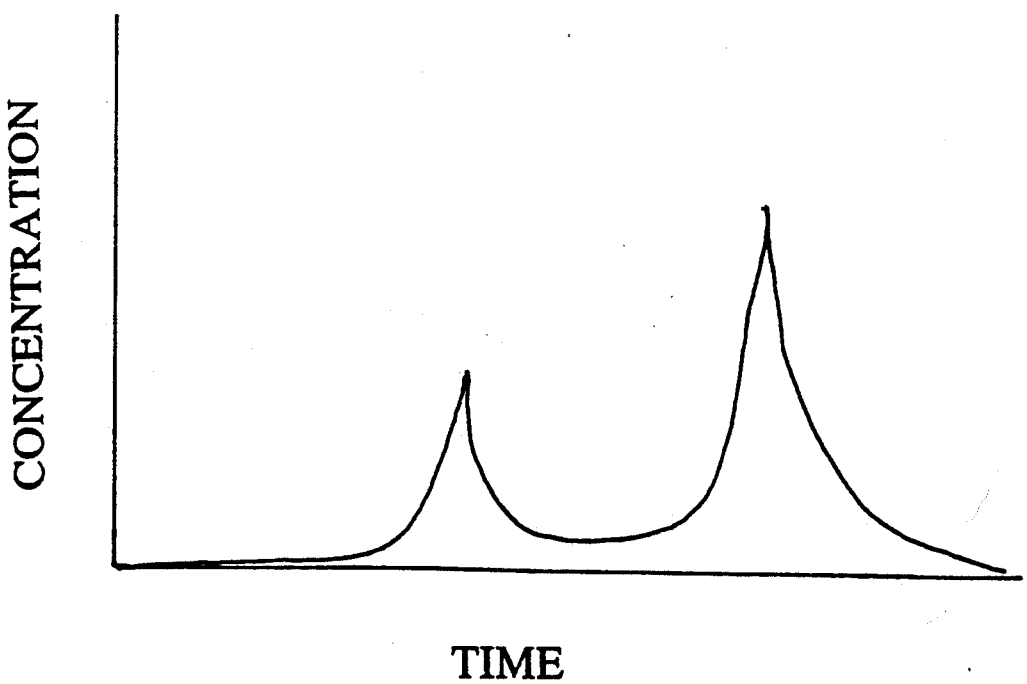
FIG. 3b is a peak diagram representative of the output using the present apparatus.

Preferably, all of the gases introduced to the apparatus 112, 212 should be clean. Sample gases which contain many constituents can create spectra with overlapping peaks, making it difficult to determine the identity of the constituents. By starting out with relatively simple sample gas and specific ion source gas, well-defined peaks will be obtained. Additionally, by pulsing the electrical drift field within the drift region 190, 290, the apparatus 121, 212 will increase the signal generated by the sample gas ions by allowing ion concentrations to build up between gating and will allow for a more precise measurement of the sample gas. As such, this apparatus 112, 212 improves the performance of any subsequent detection device, such as, for example, an ion detection or mobility means, such as a plasma chromatograph. FIG. 3a is a representative peak diagram for the current systems and FIG. 3b is a peak diagram for the same system utilizing the present apparatus 112, 212 to introduce the sample species to the measurement means.

4. Alternatives

Ion source gases can be used that only allows higher proton or electron affinity gases to be observed, or which allow the range to be extended. The ion source gas composition can be modified in order to optimize the detection of species with very low proton or electron affinities. Specific additives can be used which initiate a more complex but specific series of reactions.

The apparatus 112, 212 described may be coupled to a GC in order to introduce species from the GC to an ion detection and measurement means. In order to apply this apparatus more generally to a wide range of chemical compounds, separation by a GC of the individual sample compounds prior to being fed into the apparatus 112, 212 may be desired. This can be accomplished by coupling the sample gas introduction port B₂ of the apparatus to the outlet of a GC or the outlet of any other system converting a bulk sample into separate compounds suspended in a gas phase, including post-column derivatization devices.

When using a GC, an important factor in the present apparatus 112, 212 for real-time detection of low proton/electron affinity compounds is the selection of suitable GC column materials. It is desirable for the GC column to have an inertness towards analyte species such that no analyte loss or memory effects occur at pptrv/sub-pptrv levels. The column should achieve efficient separation of analyte species from high proton or high electron affinity compounds, and a low column bleed rendering a high signal-to-noise ratio.

The present invention also bears a high potential for a wide range of applications due to the wide range of applicability and modularity of the major peripheral instruments (GC, mass spectrometer, ion detector, mass mobility measurement means), and the relatively high electron and/or proton affinities of a large number of organic and inorganic compounds which occur in the atmosphere and in other environments. Different types of separation columns also can be used.

Other alternatives and optional apparatuses to the components of this invention include: use of other ionization sources such as corona sources or X-rays; use of multiple side or axial injection ports; and use in combination with a chromatographic system involving known variations of sample injection (e.g., gas injection valves, syringe injection) and injection ports (e.g., on-column injection, vaporization of liquids), known types of chromatographic columns (e.g., packed columns, capillary columns) and column materials, and known types of chromatographic methods (e.g., gas chromatography, supercritical fluid chromatography (SFC), liquid chromatography with devices transforming the liquid sample into a gas or fine gaseous suspension).

The above detailed description describes the best modes of the invention contemplated by the inventors at this time and is meant for illustrative purposes and not to limit the invention as defined in the appended claims.

What is claimed:

1. An apparatus for introducing ions into a detection or measurement means, comprising:
   a first section which comprises a first ionization region and a second ionization region downstream and separate from said first ionization region, means for introducing an ion source gas to said first section, means for ionizing at least a portion of said ion source gas within said first ionization region forming ion source ions, means for introducing a sample gas to said first section between said first ionization region and said second ionization region wherein said sample gas is prevented from entering said first ionization region, and means for contacting said ion source ions with at least a portion of said sample gas within said second ionization region forming sample gas ions;
   means for directing said sample gas ions from said first section to a second section and for directing any unionized portions of said ion source gas and said sample gas out of said first section; and
   said second section comprising means for introducing said sample gas ions into a detection or measurement means.

2. An apparatus as characterized in claim 1, wherein said first section further comprises an ion source ionization region and a sample gas ionization region.

3. An apparatus as characterized in claim 2, wherein said second section further comprises an ion drift region following said sample gas ionization region.

4. An apparatus as characterized in claim 3, wherein said first section comprises first gating means for directing said sample gas ions into said drift region and second gating means for directing said sample gas ions into said detection or measurement means.

5. An apparatus as characterized in claim 4, further comprising a drift gas flowing through said drift region.

6. An apparatus as characterized in claim 5, further comprising means for directing said drift gas through said drift region in the same direction as said sample gas ions.

7. An apparatus as characterized in claim 5, further comprising means for directing said drift gas through said drift region in a direction opposite to said sample gas ions.

8. An apparatus as characterized in claim 5, wherein said drift region further comprises means for increasing the concentration of said sample gas ions within said first section.

9. An apparatus as characterized in claim 4, wherein said first and second gating means separate said sample gas ions near the ion mobility of interest.

10. An apparatus as characterized in claim 2, further comprising a reaction region, comprising said sample gas ionization region and an exhaust port, whereby allowing unionized portions of said ion source gas and said sample gas to be exhausted from said apparatus resulting in an ion cluster free and reaction free drift through said drift tube region.

11. An apparatus as characterized in claim 3, wherein said drift region is contained within a tubular structural member having a cross-section of sufficient size to eliminate diffusion to the interior surface of said member.

12. An apparatus as characterized in claim 1, wherein said means for contacting said ion source ions with said sample gas is an electric field.

13. An apparatus as characterized in claim 3, further comprising a means for directing said sample gas ions into said drift region.

14. An apparatus as characterized in claim 13, wherein said means for directing said sample gas ions into said drift region is an electric field.

15. An apparatus as characterized in claim 14, wherein said means for contacting said ion source ions with said sample gas and said means for directing said sample gas ions into said drift region is said electric field.

16. An apparatus as characterized in claim 1, wherein said detection or measurement means is selected from the group consisting of ion detection and mobility measurement means.

17. A method for introducing ions into a detection or measurement means, comprising the steps of:
   (a) providing an ion source gas to a first section;
   (b) ionizing at least a portion of said ion source gas within a first reaction region in said first section to form ion source gas ions within said first section;
   (c) providing a sample gas to said first section downstream from said first reaction region;
   (d) reacting said ion source gas ions with at least a portion of said sample gas within a second reaction region in said first section separate from said first reaction region to form sample gas ions within said first section;

(e) directing said ions to a second section while simultaneously directing unionized portions of said ion source gas and said sample gas out of said first section; and (f) introducing said sample gas ions to said detection or measurement means, said detection or measurement means being located within said second section.

18. A method as characterized in claim 17, further comprising the steps of:
(c1) directing said ion source gas ions into said sample gas in said first section; and
(d1) directing said sample gas ions into a drift region within said second section.

19. A method as characterized in claim 18, further comprising the steps of:
(d2) providing a drift gas flowing through said drift region; and
(d3) gating said sample gas ions within said drift region so as to concentrate said sample gas ions.

20. A method as characterized in claim 19, wherein said drift gas flows in the same direction as said sample gas ions.

21. A method as characterized in claim 19, wherein said drift gas flows in the opposite direction as said sample gas ions.

22. A method as characterized in claim 19, further comprising the step of:
(d4) exhausting any unionized portions of said ion source gas and said sample gas, and said drift gas from said first section.

23. A method as characterized in claim 22, further comprising the step of:
(a1) purifying said ion source gas.

24. A method as characterized in claim 19, further comprising the step of:
(d2a) purifying said drift gas; subsequent to step (d2).

25. A method as characterized in claim 17 carried out at atmospheric pressure or higher.

* * * * *